(12) United States Patent
Duan

(10) Patent No.: US 6,506,853 B2
(45) Date of Patent: Jan. 14, 2003

(54) COPOLYMER COMPRISING ISOPHTHALIC ACID

(75) Inventor: Jiwen F Duan, Apex, NC (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/795,278

(22) Filed: Feb. 28, 2001

(65) Prior Publication Data

US 2002/0120094 A1 Aug. 29, 2002

(51) Int. Cl.$^7$ ............................ C08F 20/00; C08G 63/00
(52) U.S. Cl. ....................... 525/444; 528/272; 528/286; 528/301; 528/302; 528/308; 528/308.6; 525/437; 524/706; 524/710
(58) Field of Search ................................ 528/272, 286, 528/301, 302, 308, 308.6; 525/437, 444; 524/706, 710

(56) References Cited

U.S. PATENT DOCUMENTS

| | | |
|---|---|---|
| 3,196,131 A | 7/1965 | Gerwing et al. |
| 3,784,507 A | 1/1974 | Braunstein |
| 3,970,729 A | 7/1976 | Walsh et al. |
| 4,526,725 A | 7/1985 | Deardorff |
| 5,104,842 A | 4/1992 | Garapon et al. |
| 5,302,686 A | 4/1994 | Tanaka et al. |
| 5,453,479 A | 9/1995 | Borman et al. |
| 5,559,205 A | 9/1996 | Hansen et al. |
| 5,798,433 A | 8/1998 | Schmidt et al. |
| 5,922,828 A | 7/1999 | Schiraldi |
| 6,011,132 A | 1/2000 | Robertson et al. |
| 6,013,756 A | 1/2000 | Hagen et al. |
| 6,075,115 A | 6/2000 | Putzig et al. |
| 6,080,834 A | 6/2000 | Putzig et al. |
| 6,133,404 A | 10/2000 | Kang et al. |

FOREIGN PATENT DOCUMENTS

| | | |
|---|---|---|
| CS | 170813 | 1/1978 |
| CS | 170815 | 1/1978 |
| JP | 6-170911 A | 6/1994 |
| JP | 11-158260 A | 6/1999 |
| WO | WO 99/28033 A1 | 6/1999 |

OTHER PUBLICATIONS

Albright Training Manual Dated Jun. 15, 1999 and titled "The Polyethylene Terephthalte Industry".

Mondek, L and Malek, J: Kinetics of the Initaial Stage of Metal–ion Catalyzed Polyesterification of Isophthalic Acid with Ethylene Glycol; Makromolekular Chemie, Macromolucular Chemistry and Physics Col. 178, No. 8, 1977, pp. 2211–2221.

Primary Examiner—Samuel A. Acquah

(57) ABSTRACT

A substantially soluble solution of isophthalic acid in a glycol can be prepared and contacted with terephthalic acid, its ester, its oligomer, or combinations of two or more thereof. The solution can be used to incorporate isophthalic acid into polyester for bottle resins and fiber.

28 Claims, No Drawings

COPOLYMER COMPRISING ISOPHTHALIC ACID

FIELD OF THE INVENTION

This invention relates to a process for producing a substantially soluble isophthalic acid in glycol solution, to a process for using the solution in manufacturing a copolymer having repeat units derived from a carbonyl compound, isophthalic acid, and glycol, and to a process for producing the copolymer in the presence of a phosphorus compound.

BACKGROUND OF THE INVENTION

Polyesters are widely used to manufacture textile fibers and bottle resins. The largest volume polyester is polyethylene terephthalate (PET). Polypropylene terephthalate and polybutylene terephthalate are gaining importance. Polyester can be manufactured by combining a glycol such as ethylene glycol and a carbonyl compound such as dimethyl terephthalate (DMT) or terephthalic acid (TPA).

For example, DMT reacts with glycol to form bisglycolate ester of terephthalate ("monomer") in the ester exchanger column. The monomer is polymerized by condensation reactions in one or two prepolymerizers and then a final polymerizer or finisher. TPA can be combined with a glycol to form a slurry at 60 to 80° C. followed by injecting the slurry into an esterifier. Linear oligomer with degree of polymerization less than 10 is formed in one or two esterifiers at temperatures from 240° C. to 290° C. The oligomer is then polymerized in one or two prepolymerizers and then in a final polymerizer or finisher at temperatures from 250° C. to 300° C.

Additives such as catalysts, stabilizers, delusterants, and toners are often added to the DMT process before the ester exchanger, in the exchanger, or in the monomer before the prepolymerizer, or to the TPA slurry before the esterifier, in the esterifier, or in the oligomer before the prepolymerizer. Commercial polyester processes commonly use antimony compounds as polycondensation catalyst and phosphorous compounds as stabilizers. See generally, Encyclopedia of Chemical Technology, 4$^{th}$ edition, John Wiley, New York, 1994, Volume 10, pages 662–685 and Volume 19, pages 609–653.

Many commercial processes have one common esterification process or one common ester exchange process, which supplies oligomer or monomer to several continuous polymerization (CP) processes. Some of the CP processes produce polyester for fibers, while other CP processes produce polyester for packaging materials or other products. Different polyester products require different additives. In the case where one esterification process or one ester exchange process supplies several CP processes, most additives are added to the oligomer or monomer before the prepolymerizer.

Polyesters are sometimes modified with addition of a co-monomer such as isophthalic acid (IPA). For example, PET for bottle resin contains 1 to 5% IPA and 99 to 95% TPA by mole. A few PET fibers such as low-melt binders contain 10% to 45% IPA, and 90% to 55% TPA by mole, most PET for textile fiber does not contain IPA. Common practice in PET production is to have one common esterification process or ester exchange process to supply oligomer or monomer to two or more CP processes for different products, where some products need co-monomer and some do not. Currently two approaches are practiced for the addition of IPA co-monomer to PET.

One approach is to build a separate continuous esterification process to produce IPA oligomer at 240° C. to 290° C., which is injected to TPA oligomer process or DMT monomer process which is to be used for packaging materials or fibers that require IPA. The injection temperature is normally higher than 240° C. to avoid solidifying of IPA oligomer. In this approach, IPA goes to the products where it is needed. However, the separate esterification process for IPA oligomer is complicated and expensive.

Another approach is to add IPA slurry to TPA slurry or esterifier of the common esterification process. IPA slurry is generally produced by suspending IPA powder or particles in a glycol at 60° C. to 80° C. In this approach, the IPA goes to all the products whether it is desired or undesired.

Japanese Patent No. 11158260 discloses adding IPA slurry and ethylene glycol to TPA oligomer line to make copolymer. A sufficiently high flow rate of IPA slurry is required to avoid settling in the piping or injection nozzle and consequently shutting down the process. Japanese Patent No. 11209465 discloses adding a phosphorus compound to the IPA in ethylene glycol slurry and (PET) oligomer.

Therefore, there is an increasing need to develop a process for producing a substantially soluble IPA in glycol solution, which is less expensive and more flexible to operate than the known processes in manufacturing copolymer containing TPA and IPA.

SUMMARY OF THE INVENTION

A substantially soluble solution comprises isophthalic acid in a first glycol.

A process for producing a substantially soluble isophthalic acid in a first glycol solution comprises combining the isophthalic acid with the first glycol under an effective condition sufficient to substantially esterify the carboxyl group of the isophthalic acid with the glycol.

A process comprises contacting, optionally in the presence of a phosphorus compound and/or a catalyst, either (a) an isophthalic acid or substantially soluble isophthalic acid in a first glycol with a polymerization mixture comprising a carbonyl compound and a second glycol or (b) an isophthalic acid or substantially soluble isophthalic acid in a first glycol with an oligomer derived from a carbonyl compound and a second glycol under a condition effective to produce a copolymer comprising repeat units derived from the carbonyl compound or its ester, isophthalic acid and the first and/or second glycol.

DETAILED DESCRIPTION OF THE INVENTION

The term "substantially" refers to more than trivial and "substantially soluble" can mean that the concentration of insoluble isophthalic acid (IPA) in glycol is lower than 5 g, preferably lower than 2 g, and most preferably lower than 1 g per 100 g of glycol. The weight % of IPA in the solution can be in the range of from about 5% to about 75%, preferably about 5% to about 60%, more preferably 10% to 40%, and most preferably 20% to 35%, based on the total weight equaling 100%. A substantially soluble IPA in glycol solution generally remains soluble, without forming dispersion or gels, at room temperature (about 25° C.).

The preferred first glycol can have 1 to about 10, preferably 1 to about 8, and most preferably 1 to 4 carbon atoms per molecule such as, for example, an alkylene glycol, a polyalkylene glycol, alkoxylated glycol, or combinations thereof. Examples of suitable glycols include, but are not limited to ethylene glycol, propylene glycol, isopropylene glycol, butylene glycol, 1-methyl propylene glycol, pentylene glycol, diethylene glycol, triethylene glycol, polyoxyethylene glycol, polyoxypropylene glycol, polyoxybutylene glycol and combinations of two or more thereof. The most preferred glycol is ethylene glycol for it can be used in the production of a PET copolymer.

The process of the invention can be carried out by combining IPA with a glycol to form a slurry in any suitable vessel, container, or reactor. The slurry can be heated under any suitable condition effective to esterify about 50% to about 100%, preferably about 70% to about 98%, more preferably about 75% to about 95%, and most preferably 80% to 95% of the carboxyl groups in IPA, all mole %. A suitable condition can include a temperature in the range of from about 100° C. to about 250° C., preferably about 140° C. to 220° C., and most preferably 160° C. to 190° C.; a pressure that can accommodate the temperature range; and a period sufficient to substantially solubilize IPA in the glycol, generally about 1 minute to about 5 days, preferably about 10 minutes to about 2 days, and most preferably about 30 minutes to about 4 hours.

Wishing not to be bound by theory, it is believed that during the heating, the carboxyl groups in IPA are partially esterified by glycol, which is completely or substantially dissolved in glycol. This completely dissolved IPA solution can solidify or become gel when the solution is cooled.

When heated, one or two carboxyl groups of the IPA molecule can be esterified. In some cases, none is esterified. In case of IPA in ethylene glycol, the substantially soluble solution can contain bis(hydroxyethyl)isophthalate or dihydroxyethyl isophthalate, monoesterified IPA, unesterfied IPA, ethylene glycol, and water as shown below.

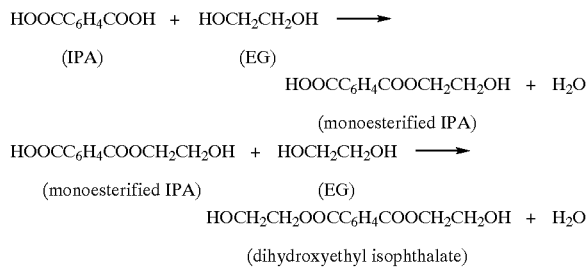

Dimers, trimers, and tetramers of esterified IPA can also form as the reactions continue. For example, bis(hydroxyethyl)isophthalate, bis(hydroxypropyl) isophthalate, bis(hydroxybutyl)isophthalate, or combinations thereof can be formed. At the end of heating, the IPA solution can be cooled by stopping the heat or cooled by any means known to one skilled in the art such as heat exchanger. The water generated can be kept in the solution, or partially or fully evaporated and condensed.

It is preferred that the substantially soluble IPA solution remains clear when cooled to room temperature. When the percentage of esterified carboxyl groups is below 70% by mole, the solution may solidify or become partially gelled at room temperature, especially at higher original concentrations of IPA in glycol such as 40% to 50% (by weight) IPA.

When the percentage of esterified carboxyl groups is higher than 95% by mole, dimer, trimer, tetramer, and oligomer may form, which are dissolved in the solution at high temperature but precipitate as solids in the solution at room temperature, which may affect fluidity of the solution. If the original concentration of IPA in glycol is high such as at 40% to 50% by weight and the percentage of esterified carboxyl groups is higher than 95% by mole, the solution may contain gels from dimer, trimer, and oligomer at room temperature, which may affect fluidity of the solution. Those IPA solutions that solidify or form gel at room temperature can become clear solution again and be injected into TPA oligomer when heated.

The invention process can be a batch process that is simple and inexpensive to operate. It can also be carried out by any continuously methods known to one skilled in the art.

According to the invention, a catalyst can be present in the process to facilitate the production of a substantially soluble IPA solution. Any catalyst known to esterify a carbonyl compound can be used. The catalyst can be a cobalt, antimony, manganese, or zinc catalyst commonly employed in the manufacture of polyester, description of which is omitted herein because such catalyst is well-known to one skilled in the art. The catalyst composition also can comprise a titanium compound.

A preferred antimony compound can be any antimony compound that is substantially soluble in a solvent disclosed above. Examples of suitable antimony compounds include, but are not limited to, antimony oxides, antimony acetate, antimony hydroxides, antimony halides, antimony sulfides, antimony carboxylates, antimony ethers, antimony glycolates, antimony alcoholates, antimony nitrates, antimony sulfates, antimony phosphates, and combinations of two or more thereof.

According to the invention, the preferred titanium compounds used in component are tetraalkyl titanates, also referred to as titanium tetrahydrocarbyloxides for they are readily available and effective. Examples of suitable tetraalkyl titanates include those having the formula of $Ti(OR)_4$ where each R is individually selected from an alkyl, cycloalkyl, alkaryl, hydrocarbyl radical containing from 1 to about 30, preferably 2 to about 18, and most preferably 2 to 12 carbon atoms per radical and each R can be the same or different. Titanium tetrahydrocarbyloxides in which the hydrocarboxyl group contains from 2 to about 12 carbon atoms per radical which is a linear or branched alkyl radical are most preferred because they are relatively inexpensive, more readily available, and effective in forming the solution. Suitable tetraalkyl titanates include, but are not limited to, titanium tetraethoxide, titanium tetrapropoxide, titanium tetraisopropoxide, titanium tetra-n-butoxide, titanium tetrahexoxide, titanium tetra 2-ethylhexoxide, titanium tetraoctoxide, and combinations of two or more thereof. The titanium tetrahydrocarbyloxides are well known to one skilled in the art. See, for example, U.S. Pat. Nos. 6,066,714 and 6,166,170, the description of which is incorporated herein by reference. Examples of commercially available organic titanium compounds include, but are not limited to, TYZOR® TPT and TYZOR® TBT (tetra isopropyl titanate and tetra n-butyl titanate, respectively) available from E. I. du Pont de Nemours and Company, Wilmington, Del., U.S.A.

A titanium-containing composition can be produced by any means known to one skilled in the art such as those disclosed in U.S. Pat. No. 6,066,714 and U.S. Pat. No. 6,166,170 discussed above and description of which is omitted herein for the interest of brevity.

The catalyst, expressed as element Co, Sb, Mn, Zn, or Ti, can be present in the range of about 0.001 to about 30,000 part per million by weight (ppm) of a combination comprising glycol and IPA.

According to another embodiment of the invention, an esterification, transesterification, or polymerization process can comprise contacting, optionally in the presence of a phosphorus compound and/or a catalyst, either (a) an isophthalic acid or substantially soluble isophthalic acid in a first glycol with a polymerization mixture comprising a carbonyl compound and a second glycol or (b) an isophthalic acid or substantially soluble isophthalic acid in a first glycol with an oligomer derived from a carbonyl compound and a second glycol under a condition effective to produce a copolymer comprising repeat units derived from the terephthalic acid or its ester, isophthalic acid, first glycol, and second glycol.

The catalyst and partially esterified IPA can be the same as those disclosed above and the disclosures of which are incorporated here. The second glycol can be the same or different from the first glycol and can include those disclosed above for the first glycol. The presently preferred second glycol is ethylene glycol or 1,3-propanediol (propylene glycol).

The catalyst, expressed as element Co, Sb, Mn, Zn, or Ti, can be present in the range of about 0.001 to about 30,000 ppm of the medium comprising the carbonyl compound and glycol, preferably about 0.1 to about 1,000 ppm, and most preferably 1 to 100 ppm by weight. A cocatalyst, if present, can be in the range of from about 0.01 to about 1,000 ppm of the reaction medium.

For example, a titanium catalyst, alone or with other catalyst such as antimony and/or cobalt can be used as polycondensation catalyst. Alternatively, a titanium-containing catalyst can be present in the ester exchanger to accelerate transesterification reaction or in the esterifier to accelerate the esterification reaction. Generally, titanium-containing catalyst is more active in polycondensation reaction than in esterification or transesterification. The proper level of titanium-containing catalyst for esterification or transesterification can be an excess level for polycondensation. When titanium-containing catalyst presented in the esterifier or ester exchanger (transesterifier) is an excess for polycondensation, or when polycondensation is intended with a non titanium-containing catalyst such as antimony, part of or all of the titanium catalyst is preferably deactivated or inhibited after esterification or transesterification with a phosphorus compound disclosed above, to avoid discoloration of the polymer.

The titanium-containing catalyst present in the polymer can cause increased degradation and yellowness in the future processing. Part of or all of the titanium catalyst can be deactivated or inhibited after polymerization with a phosphorus compound disclosed below, to avoid discoloration of the polymer.

Similarly, when manganese, zinc, cobalt, or other catalysts are used as esterification or transesterification catalyst and titanium-containing catalyst is used as polycondensation catalyst, these catalysts can be deactivated by the presence of a phosphorous compound disclosed above.

Any carbonyl compound which, when combined with a glycol, can produce a polyester can be used. Such carbonyl compounds include, but are not limited to, acids, esters, amides, acid anhydrides, acid halides, salts of carboxylic acid, oligomers or polymers having repeat units derived from an acid, or combinations of two or more thereof. The presently preferred acid is an organic acid such as a carboxylic acid or ester thereof. The oligomer of a carbonyl compound such as TPA and glycol generally has a total of about 2 to about 100, preferably from about 2 to about 20 repeat units derived from the carbonyl compound and glycol.

The organic acid or ester thereof can have the formula of $R^2O_2CACO_2R^2$ in which each $R^2$ independently can be (1) hydrogen, or (2) hydrocarbyl radical in which each radical has 1 to about 30, preferably about 3 to about 15 carbon atoms per radical which can be alkyl, alkenyl, aryl, alkaryl, aralkyl radical, or combinations of two or more thereof, and in which A is an alkylene group, an arylene group, alkenylene group, or combinations of two or more thereof. Each A has about 2 to about 30, preferably about 3 to about 25, more preferably about 4 to about 20, and most preferably 4 to 15 carbon atoms per group. Examples of suitable organic acids include, but are not limited to, terephthalic acid, isophthalic acid, napthalic acid, succinic acid, adipic acid, phthalic acid, glutaric acid, oxalic acid, and combinations of two or more thereof. Examples of suitable esters include, but are not limited to, dimethyl adipate, dimethyl phthalate, dimethyl terephthalate, dimethyl glutarate, and combinations of two or more thereof. The preferred organic acid is terephthalic acid or its ester dimethyl terephthalate The molar ratio of the glycol (including first glycol and second glycol) to carbonyl compound can be any ratio so long as the ratio can effect the production of an ester or polyester. Generally the ratio can be in the range of from about 1:1 to about 10:1, preferably about 1:1 to about 5:1, and most preferably 1:1 to 4:1.

The invention process can also be carried out in any suitable means using any of the conventional melt or solid state techniques and in the presence or absence of a toner compound to reduce the color of a polyester produced. Example of toner compounds include, but are not limit to, cobalt aluminate, cobalt acetate, Carbazole violet (commercially available from Hoechst-Celanese, Coventry, R.I., U.S.A., or from Sun Chemical Corp, Cincinnati, Ohio, U.S.A.), Estofil Blue S-RLS® and Solvent Blue 45™ (from Sandoz Chemicals, Charlotte, N.C., U.S.A), CuPc Blue (from Sun Chemical Corp, Cincinnati, Ohio, U.S.A.). These toner compounds are well known to one skilled in the art and the description of which is omitted herein. The toner compound can be used with the catalyst disclosed herein in the amount of about 0.1 ppm to 1000 ppm, preferably about 1 ppm to about 100 ppm, based on the weight of polyester produced.

The invention process can also be carried out using any of the conventional melt or solid state techniques and in the presence or absence of an optical brightening compound to reduce the yellowness of the polyester produced. Example of optical brightening compounds include, but are not limit to, 7-naphthotriazinyl-3-phenylcoumarin (commercial name "Leucopure EGM", from Sandoz Chemicals, Charlotte, N.C., U.S.A.), 4,4'-bis(2-benzoxazolyl) stilbene (commercial name "Eastobrite", from Eastman Chemical, Kingsport, Tenn., U.S.A.). These optical brightening compounds are well known to one skilled in the art and the description of which is omitted herein. The optical brightening compound can be used with the catalyst disclosed herein in the amount of about 0.1 ppm to 10000 ppm, preferably about 1 ppm to about 1000 ppm, based on the weight of polyester produced.

The oligomer of a carbonyl compound such as terephthalic acid can be produced by contacting terephthalic acid, its ester, or combinations thereof with a second glycol under an esterification, transesterification, or polymerization conditions well known to one skilled in the art to produce a total of about 2 to about 100, preferably from about 2 to about 20 repeat units derived from the terephthalic acid and glycol.

A suitable condition to effect the production of a polyester can include a temperature in the range of from about 150° C. to about 500° C., preferably about 200° C. to about 400° C., and most preferably 250° C. to 300° C. under a pressure in the range of from about 0.001 to about 1 atmosphere (0.1 to 101.3 kPa) for a time period of from about 0.2 to about 20, preferably about 0.3 to about 15, and most preferably 0.5 to 10 hours.

The quantity of the IPA or partially esterified IPA solution can be any desired quantity such that the resulting copolymer can have a molar ratio of IPA to terephthalic acid in the range of from about 0.1:99.9 to about 60:40, preferably about 0.1:99.9 to about 45:55.

According to the invention, a phosphorus compound can be present in the IPA solution before, during, or after the carboxyl groups of IPA are esterified. Alternatively, the phosphorus compound can be present in the process before, during, or after carbonyl compound or ester thereof is esterified or transesterified. Similarly, it can be present before, during, or after the polycondensation stage.

The phosphorus compound can be used to inhibit the catalytic activity of a titanium-containing catalyst, to reduce the discoloration of polyester produced using a titanium-containing catalyst, or both. The phosphorus compound can also be used to inhibit the catalytic activity of other metal-containing catalyst such as cobalt, zinc, and manganese, to reduce the discoloration of polyester produced using these catalysts, or both. Similarly, the phosphorus compound can be used to inhibit the catalytic activity of trace metals presented in raw materials, such as aluminum and silicon, to reduce the discoloration of polyester produced with these trace metals, or both.

The phosphorus compound can be mixed with the catalyst, such as titanium, antimony, manganese, zinc, before the catalyst is introduced to the polyester reaction process. Alternatively, the phosphorous compound can be introduced to the process separately before or after the catalyst is introduced.

A phosphorus compound that can be used with a polyester catalyst to produce polyester having low yellowness, as compared to a polyester produced from a catalyst without such phosphorus compound can be used. Examples of suitable phosphorus compounds include, but are not limited to, phosphoric acid or salts thereof, phosphorous acid or salts thereof, a polyphosphoric acid or a salt thereof, a phosphonate ester, a pyrophosphoric acid or salt thereof, a pyrophosphorous acid or salt thereof, and combinations of two or more thereof. The polyphosphoric acid can have the formula of $H_{n+2}P_nO_{3n+1}$ in which n is $\geq 2$. The phosphonate ester can have the formula of $(R^1O)_2P(O)ZCO_2R^1$ in which each $R^1$ can be the same or different and can be independently H, $C_{1-4}$ alkyl, or combinations thereof; and Z is $C_{1-5}$ alkylene, $C_{1-5}$ alkylidene, or combinations thereof, di(polyoxyethylene) hydroxymethyl phosphonate, and combinations of two or more thereof. The salt can be an alkali metal salt, alkaline earth metal salt, ammonium salt, or combinations of two or more thereof.

Illustrative examples of suitable phosphorus compounds include, but are not limited to, phosphoric acid, phosphorous acid, sodium phosphate, potassium phosphate, sodium phosphite, potassium phosphite, potassium tripolyphosphate, sodium tripolyphosphate, potassium tetra phosphate, sodium pentapolyphosphate, sodium hexapolyphosphate, potassium pyrophosphate, potassium pyrophosphite, sodium pyrophosphate, sodium pyrophosphate decahydrate, sodium pyrophosphite, ethyl phosphonate, propyl phosphonate, hydroxymethyl phosphonate, di(polyoxyethylene) hydroxymethyl phosphonate, methylphosphonoacetate, ethyl methylphosphonoacetate, methyl ethylphosphonoacetate, ethyl ethylphosphonoacetate, propyl dimethylphosphonoacetate, methyl diethylphosphonoacetate, triethyl phosphonoacetate, or combinations of two or more thereof.

A titanium-containing catalyst present in polyester can cause increased degradation and yellowness in the future processing. Part of or all of the titanium catalyst can be deactivated or inhibited after polymerization with a phosphorous compound disclosed above in composition component, to avoid discoloration of the polymer.

Similarly, when manganese, zinc, or other catalysts are used as esterification or transesterification catalyst and titanium-containing catalyst is used as polycondensation catalyst, these catalysts can be deactivated by the presence of a phosphorous compound disclosed above.

EXAMPLES

The following examples are included to further illustrate the invention and are not to be construed as to unduly limit the scope of the invention.

The number of carboxyl groups COOH before esterification was calculated from concentration and chemical formula. The number of carboxyl groups COOH in the partially esterified IPA solution was determined as follows. A weighed specimen was dissolved in o-cresol, diluted with chloroform and titrated with methanolic potassium hydroxide to a bromophenol blue end point. The end point was determined colorimetrically at 600 nm using a recording titrator.

Water content by weight in the partially esterified IPA solution was determined by the Karl Fisher method. Water was converted stochimetrically in the presence of sulfur dioxide, methanol and suitable base of addition iodine. The titration was followed by a two-pin platinum electrode having a current source applied to its poles. The voltage measured at the polarized electrode pins was used by the control as an input signal. When the last trace of water was titrated out, voltage dropped to virtually zero. The electrodes were then depolarized by the iodine now present; the small electrical current oxides iodine at one electrode and reduces the amount of iodine at the other electrode.

Diethylene glycol (DEG) in IPA solution was analyzed in the same way as DEG in polymer which requires depolymerization. The samples were treated with 2-aminoethanol (2AE) containing benzyl alcohol (BA) as an internal standard. The reaction mixture was diluted with isopropyl glycol and injected into a gas chromatograph. The ratio of the areas of the DEG and BA peaks, corrected for the sample weight, was translated by a calibration factor into weight percent DEG.

Example 1

This example shows the production of a clear solution of IPA in ethylene glycol.

Ethylene glycol (EG; 360 g) and IPA (240 g) were added to a kettle, that has been nitrogen purged to substantially remove air and moisture to the vent, to produce a mixture containing approximately 40% IPA by weight. The mixture was heated from about 25° C. (room temperature) to 180° C. in 110 minutes. Boiling started at 174° C. after 50 minutes starting heat, boiling stopped after 1 hour at 180° C., total boiling time was 2 hours. IPA was completely dissolved when the temperature reached 180° C. A sample was taken at that time. The clear solution sample solidified immediately when cooled to about 25° C. (room temperature).

The solution was further heated at 180° C. for additional 2 hours. A sample taken at this time remained clear when cooled to room temperature. Carboxyl groups were analyzed to be 603 meq/kg (88.5% of IPA COOH were esterified). It also contained diethylene glycol (DEG) 0.51% and water 1.33%.

Upon heating for a total of 4 hours at 180° C., a clear solution sample taken became a liquid containing partial gels when cooled to room temperature. Analysis showed: Carboxyl groups, 418 meq/kg (92.0% of IPA COOH were esterified): DEG, 0.74%; and water, 1.19%.

When this solution was heated for a total of 6 hours at 180° C., the clear liquid became a gel when cooled to room temperature. Carboxyl groups were analyzed to be 236 meq/kg (95.6% of IPA COOH were esterified), DEG 0.90% and water 0.78%.

The results show that solution having 80% to 90% by mole of the IPA carboxyl groups esterified remained clear solution upon cooling to room temperature. Though clear solution at room temperature is not required for daily operation because the IPA solution is normally injected into TPA oligomer line at higher temperatures, clear IPA solution at room temperature would not plug any piping or equipment in case of temporarily equipment or process failures that cause the solution to cool to ambient temperature.

Example 2

This example shows that the invention IPA solution can contain an antimony compound to reduce glycol injection in CP process.

EG (360 g) and IPA (240 g) were added to a kettle, as in Example 1, to make a mixture containing approximately 40% IPA. It took 30 minutes to heat the mixture from about 25° C. to 180° C. Boiling started at 180° C. after 30 minutes starting heat, boiling stopped after 75 minutes at 180° C., total boiling time was 75 minutes. IPA was completely dissolved after the solution was heated at 1 80° C. for 75 minutes.

A sample was taken after heating at 180° C. for 2 hours. The clear solution sample became gel when cooled to room temperature. Another sample was taken after heating at 180° C. for 4 hours. The sample remained clear solution when cooled to room temperature. Analysis showed: Carboxyl groups, 899 meq/kg (82.9% of IPA COOH esterified); DEG, 0.50%; and water, 1.10%.

Antimony oxide ($Sb_2O_3$; 5.02 g) was added at the end of 4-hour heating at 180° C. to the solution. The $Sb_2O_3$ dissolved immediately, antimony in the solution did not crystallize or precipitate when the solution was cooled to room temperature. Antimony in the solution was 0.7%, if this solution were injected to TPA oligomer to make polymer containing 2% IPA by mole, antimony input would be 300 ppm of polymer. Antimony in IPA solution can be increased or decreased to meet catalyst needs.

Example 3

This example illustrates that a titanium compound can be added to the IPA solution to accelerate esterification reaction.

EG (480 g), IPA (120 g), and tetraisopropyl titanate (TPT; 0.2136 g) were added to a kettle as in Example 1 to produce a mixture containing 20% IPA and 60 ppm Ti (by weight). It took 40 minutes to heat it from about 25° C. to 180° C. IPA was completely dissolved when the temperature reached 180° C., a sample was taken at that time, the clear solution sample solidified immediately when cooled to room temperature. Analysis showed: Carboxyl groups, 884 meq/kg (64% of IPA COOH were esterified).

After heating at 180° C. for 2 hours, a sample was taken, the clear solution sample remained clear when cooled to room temperature. Analysis showed: Carboxyl groups, 539 meq/kg (78.5% of IPA COOH were esterified); DEG, 0.183%; and water 1.49%.

After heating at 180° C. for 4 hours, a sample was taken, the clear solution remained clear when cooled to room temperature. Analysis showed: Carboxyl groups, 249 meq/kg (90.1% of IPA COOH were esterified); DEG, 0.372%; and water, 0.88%.

After heating at 180° C. for 6 hours, the liquid contained some white solids when cooled to room temperature. Analysis showed: Carboxyl groups, 91 meq/kg (96.4% of IPA COOH were esterified); DEG, 0.622%; and water, 0.51 %.

Example 4

This example shows that lower temperature requires longer heating time.

EG (480 g), IPA (120 g), and TPT (0.2136 g) were added to a kettle as in Example 1. The mixture contained approximately 20% IPA and 60 ppm Ti. It took 40 minutes to heat it from about 25° C. to 160° C. IPA was completely dissolved after 80 minutes at 160° C., a sample was taken at that time, the clear solution sample solidified immediately when cooled to room temperature.

After heating at 160° C. for 4 hours, a sample was taken. The clear sample solution became gel when cooled to room temperature. Analysis showed: Carboxyl groups, 685 meq/kg (72.5% of IPA COOH esterified); DEG, 0.091%; water, 1.50%.

After heating at 160° C. for 6 hours, the clear solution remained clear when cooled to room temperature. Analysis showed: Carboxyl groups, 553 meq/kg (78.0% of IPA COOH esterified); DEG 0.137%; and water 1.95%.

Example 5

This example shows the production of a clear solution of IPA in 1,3-propanediol (propylene glycol; PG).

PG (480 g) and IPA (120 g) were added to a kettle, as in Example 1, to produce a mixture containing approximately 20% IPA by weight. The mixture was heated from room temperature to 180° C. in 15 minutes. After 15 minutes at 180° C., boiling stopped, IPA completely dissolved.

A sample was taken after 4 hours at 180° C., analysis showed: Carboxyl groups, 198 meq/kg (92.1% of IPA COOH esterified), water 1.12%.

After 6 hours at 180° C., the solution was cooled. The solution remained as clear golden brown liquid without any solids at room temperature. Analysis showed: Carboxyl groups, 152 meq/kg (94.0% of IPA COOH esterified); and water, 0.69%.

Example 6

This example shows the mass balance of the invention solution due to evaporation of water.

EG (378.8 g) and IPA (222.2 g) were added to a kettle, as in Example 1. The vapor was condensed in a two-stage condensing system with dry ice. Seventy minutes after heating started from about 25° C., the mixture began to boil at 177° C. It reached 180° C. in 20 minutes, and was maintained at 180° C. thereafter. The mixture became clear solution in about 45 minutes after boiling started. Total boiling time was about 1 hour. The solution was maintained at 180° C. for 3.3 hours after boiling stopped. Then the solution was cooled to room temperature by stopping heating. The cooled solution was clear except a small amount of white movable solids in the bottom. The weight of solution in the kettle was 548 grams, the condensed vapor was 35 grams. Analysis of the solution showed: Carboxyl groups, 776 meq/kg (84% of IPA COOH esterified); DEG, 0.34%; and water, 0.81%.

Example 7

This example shows an IPA solution containing phosphoric acid.

EG (337.0 g), IPA (222.2 g), $H_3PO_4$ solution ($H_3PO_4$ 10%, ethylene glycol 88.2%, water 1.8%, all by weight; 40.8 g) were added to a kettle, as in Example 6. Forty minutes after heating started from about 25° C., the mixture began to boil at 177° C. It reached 180° C. in 15 minutes, and was maintained at about 180°. The mixture became clear solution after 15 minutes at about 180° C. Boiling stopped after 80 minutes at 180° C. The solution was maintained at 180° C. for 3 hours after boiling stopped. Then the solution was cooled to room temperature by stopping heating, the cool solution was clear without solids. The weight of solution in the kettle was 524.9 g, the condensed vapor 46.1 g.

Example 8

This example illustrates a continuous polymerization process for polyester with a polymer flow rate of 55 kg/hour. Tetraisopropyl titanate (TPT) was used as catalyst to accelerate the esterification reaction.

EG (181.4 kg), IPA (45.4 kg), and TPT (53.8 g) were added into a mix tank, which had been nitrogen purged and an open discharge port to remove water vapor. The mixture contained about 20% IPA and 40 ppm Ti. It took 60 minutes to heat the mixture from 42° C. to 185.5° C. IPA was completely dissolved at about 180° C.

After heating at about 182.7° C. for 4 hours, heating was stopped. Sample was taken 8 hours later when the solution in the mix tank was cooled to 120° C. Analysis showed: Carboxyl groups, 115 meq/kg (95.4% of IPA COOH esterified); DEG, 1.10%; and water, 2.43%. The liquid sample contained a small amount of white solids when cooled to room temperature.

The solution was injected from feed tank into TPA oligomer in the pilot plant to make copolymer containing 98% TPA and 2% IPA by mole. Antimony glycolate and cobalt acetate were injected into oligomer line as catalyst at a rate of 230 ppm Sb and 48.7 ppm Co in polymer. To reduce the interaction with antimony and cobalt, phosphoric acid was injected into the TPA esterifier at a rate of 30 ppm P in polymer. The esterifier was run at 282° C., the first prepolymerizer ("flasher") was 265° C. at vacuum 90 mm Hg (12 kPa), the second prepolymerizer was 275° C. at vacuum 35 mm Hg (4.67 kPa), the final polymerizer ("finisher") temperature was 282° C. Finisher pressure was controlled by an online melt viscosity instrument which measures polymer molecular weight. In this example, the average of finisher pressure was 4.28 mm Hg (0.57 kPa). Polymer temperature in the transfer line from finisher to casting machine was 282° C. The molten polymer was cast with cooling water and cut to obtain flake of 0.44 g per 25 particles.

The polymerization process performed very well, the polymer resin had high quality: Intrinsic viscosity 0.638, turbidity 110.5, acetaldehyde 42.6 ppm, melting point 249.5° C., L color 52.02, a color 0.844, b color −1.18.

Intrinsic viscosity (I.V.) analysis was determined as follows. Weighed polymer sample was dissolved in hexafluoroisopropanol (HFIP) to make 4.75% solution. The drop time of the solution at 25° C. was measured using a constant volume viscometer in an Octavisc® auto viscometer system. Turbidity was a measure of cloudiness in polymer resin and was determined by dissolving a weighed flake sample in HFIP followed by reading with a Hach Model 2100 AN Turbidimeter. The lower the turbidity number, the clear the polymer was.

Acetaldehyde was measured as follows. Four (4) grams of polymer was added to a cryogrinding tube. The tube was cooled in liquid nitrogen for 1.5 minutes. It was then impact ground for 3 minutes, and cooled to room temperature for 90 minutes. About 1 g of material was charged to a 22 ml headspace vial and sealed; the weight was recorded. The sample was then injected with a Hewlett Packard HP 7694 automated headspace sampler, which was coupled to Hewlett Packard 5890 gas Chromatograph instrument. The injector temperature was 160° C., the detector temperature was 250° C., column was DB-wax with ID 0.53 mm, length 30 meters, 1.0 micron film thickness, the detector type was flame ionization. Acetaldehyde concentration was calculated from the area comparing to a standard.

Color of the resulting oligomer and any polymer produced therefrom was measured in terms of the L-value and b-value, using a Hunter color instrument.

The L-value shows brightness, with the greater the numerical value showing higher (desirable) brightness. The b-value shows the degree of yellowness, with a higher numerical value showing a higher (undesirable) degree of yellowness.

Example 9

This example shows that phosphonate ester reduces insoluble solids in polymer thereby reducing polymer turbidity and improve polymer color. Titanium catalyst was added to accelerate esterification reaction in IPA solution.

EG (181.4 kg), IPA (45.4 kg), and TPT (53.8 g) were added into a mix tank, which had nitrogen purge and an open discharge port to remove water vapor.

The mixture contained about 20% IPA and 40 ppm Ti. It took 60 minutes to heat the mixture from 36° C. to 181.5° C. IPA was completely dissolved at about 180° C.

After heating at about 180.8° C. for 4.5 hours, heating was stopped. Sample was taken 11 hours later when the solution in the mix tank was cooled to 116° C. Analysis showed: Carboxyl groups, 111 meq/kg (95.6% of IPA COOH esterified); DEG, 0.929%; and water, 0.91%. The liquid sample contained some white solids when cooled to room temp.

The pilot plant polymerization process and operating conditions were the same as Example 8. Ingredients were the same as Example 7 except that phosphoric acid was replaced with triethyl phosphonoacetate (TEPA) in glycol solution at a rate of 30 ppm P in polymer. TEPA in glycol solution containing phosphorous 0.158% by weight was made by mixing ethylene glycol (81.6 kg) and TEPA (0.947 kg).

The average of finisher pressure was 3.37 mm Hg (0.45 kPa). The polymer resin had lower turbidity (better), higher L color (better), and lower b color (better) than the polymer in Example 7: Intrinsic viscosity 0.637, turbidity 80.5, acetaldehyde 23.3 ppm, melting point 249.6° C., L color 53.15, a color 0.916, b color −2.166.

Example 10

This example shows a polymerization test in the same pilot plant as Example 8. No titanium catalyst was added to the IPA solution, the degree of esterification in the solution was lower.

EG (181.4 kg) and IPA (45.4 kg) were added in a mix tank, which had nitrogen purge and an open discharge port to remove water vapor. The mixture contained IPA about 20%. It took 2 hours to heat the mixture from 35° C. to 178.2° C. IPA was completely dissolved then.

After heating at about 180.5° C. for 4 hours, heating was stopped. Sample was taken 11 hours later when the solution in the mix tank was cooled to 100° C. Analysis showed: Carboxyl groups, 329 meq/kg (86.9% of IPA COOH were esterified); DEG, 0.939%; and water, 1.86%. The IPA solution sample remained clear when cooled to room temperature.

In the feed tank solution temperature decreased to 60~80° C. The solution was injected from feed tank into TPA oligomer to make copolymer containing 98% TPA and 2% IPA. Additives, process conditions, and polymer properties were similar to Example 8, except that injected cobalt was 44.9 ppm of polymer, injected phosphorous from TEPA was 40 ppm of polymer. Compared with Example 8, without the small amount of titanium catalyst (Ti 3.4 ppm of polymer) in IPA solution, polymer color was slightly better. The average of finisher pressure was 3.45 mm Hg (0.46 kPa). The polymer had intrinsic viscosity 0.637,, turbidity 59.1, acetaldehyde 36.1 ppm, melting point 250.2° C., L color 54.44, a color 0.785, b color –2.165.

What is claimed is:

1. A solution comprising isophthalic acid and a glycol wherein said isophthalic acid is substantially soluble in said glycol and has about 75 to about 95 mole % of its carboxylic group esterified by said glycol.

2. A solution according to claim 1 wherein the concentration of said isophthalic acid in said glycol is in the range of from 5% to 60% by weight.

3. A solution according to claim 1 wherein the concentration of said isophthalic acid in said glycol is in the range of from 10% to 40% by weight.

4. A solution according to claim 1 wherein the concentration of said isophthalic acid in said glycol is in the range of from 10% to 40% by weight.

5. A process comprising combining a glycol and isophthalic acid to form a mixture and heating said mixture under a condition sufficient to substantially dissolve said isophthalic acid to produce a substantially soluble solution wherein said isophthalic acid has about 75 to about 95 mole % of its carboxylic group esterified by said glycol.

6. A process according to claim 5 wherein said isophthalic acid has about 80 to about 95 mole % of its carboxylic group esterified by said glycol.

7. A process according to claim 6 further comprising cooling said solution to a temperature substantially lower than the temperature for substantially dissolving said isophthalic acid.

8. A process according to claim 6 wherein said solution comprises monoesterified IPA, dihydroxyethyl isophthalate, dimer thereof, trimer thereof, tetramer thereof, oligomer thereof, or combinations of two or more thereof.

9. A process according to claim 5 wherein the concentration of said isophthalic acid in said glycol is in the range of from 5% to 60% by weight.

10. A process according to claim 6 wherein the concentration of said isophthalic acid in said glycol is in the range of from 10% to 40% by weight.

11. A process according to claim 5 wherein said mixture is heated to a temperature in the range of 100° C. to about 250° C.

12. A process according to claim 5 wherein said mixture is heated to a temperature in the range of 160° C. to 190° C.

13. A process comprising contacting either (a) a substantially soluble isophthalic acid in a first glycol with a polymerization mixture comprising a carbonyl compound and a second glycol or (b) a substantially soluble isophthalic acid in a first glycol with an oligomer derived from a carbonyl compound and a second glycol under a condition effective to produce a copolymer comprising repeat units derived from said carbonyl compound or ester thereof, isophthalic acid, the first glycol, and second glycol wherein said isophthalic acid in said substantially soluble solution has about 75 to about 95 % mole of its carboxylic group esterified by said glycol.

14. A process according to claim 13 wherein
    said carbonyl compound is selected from the group consisting of terephthalic acid, isophthalic acid, napthalic acid, succinic acid, adipic acid, phthalic acid, glutaric acid, oxalic acid, dimethyl adipate, dimethyl phthalate, dimethyl terephthalate, dimethyl glutarate, oligomer thereof, and combinations of two or more thereof, and
    said first glycol and second glycol are each independently selected from the group consisting of ethylene glycol, propylene glycol, isopropylene glycol, butylene glycol, 1-methyl propylene glycol, pentylene glycol, diethylene glycol, triethylene glycol, polyoxyethylene glycol, polyoxypropylene glycol, polyoxybutylene glycol, and combinations of two or more thereof, and 15. A process according to claim 13 wherein said carbonyl compound is terephthalic acid, ester thereof, oligomer thereof, or combinations of two or more thereof and said first glycol and second glycol are each ethylene glycol.

16. A process according to claim 15, wherein the mole ratio of terephthalate and isophthalate in said copolymer is 99.1:0.1 to 50:50.

17. A process comprising contacting, in the presence of a phosphorus compound, either (a) an isophthalic acid or substantially soluble isophthalic acid in a first glycol with a polymerization mixture comprising a carbonyl compound and a second glycol or (b) an isophthalic acid or substantially soluble isophthalic acid in a first glycol with an oligomer derived from a carbonyl compound and a second glycol under a condition effective to produce a copolymer comprising repeat units derived from said carbonyl compound or ester thereof, isophthalic acid, the first glycol, and second glycol wherein said phosphorus compound is selected from the group consisting of phosphorous acid or a salt thereof, a polyphosphoric acid or a salt thereof, a phosphonate ester, a pyrophosphoric acid or salt thereof, a pyrophosphorous acid or salt thereof, and combinations of two or more thereof and said phosphorus compound is introduced into (a) or (b) together with or separate from a catalyst composition.

18. A process according to claim 17 wherein said polyphosphoric acid has the formula of $H_{n+2}P_nO_{3n+1}$; said phosphonate ester is selected from the group consisting of $(R^1O)_2P(O)ZCO_2R^1$, di(polyoxyethylene) hydroxymethyl phosphonate, and combinations thereof; n is $\geq 2$; each $R^1$ is independently selected from the group consisting of H, $C_{1-4}$ alkyl, and combinations thereof; and Z is selected from the group consisting of $C_{1-5}$ alkylene, $C_{1-5}$ alkylidene, and combinations thereof.

19. A process according to claim 17 wherein said phosphorus compound is selected from the group consisting of, phosphorous acid, sodium phosphite, potassium phosphite, potassium tripolyphosphate, sodium tripolyphosphate, potassium tetrapolyphosphate, sodium pentapolyphosphate, sodium hexapolyphosphate, potassium pyrophosphate, potassium pyrophosphite, sodium pyrophosphate, sodium pyrophosphite, ethyl phosphonate, propyl phosphonate, hydroxymethyl phosphonate, di(polyoxyethylene) hydroxymethyl phosphonate, methylphosphonoacetate, ethyl methylphosphonoacetate, methyl ethylphosphonoacetate, ethyl ethylphosphonoacetate, propyl dimethylphosphonoacetate, methyl diethylphosphonoacetate, triethyl phosphonoacetate, and combinations of two or more thereof.

20. A process according to claim 17 wherein said phosphorus compound is phosphorous acid, potassium tripolyphosphate, sodium tripolyphosphate, potassium pyrophosphate, sodium pyrophosphate, di(polyoxyethylene) hydroxymethyl phosphonate, or triethyl phosphonoacetate.

21. A process according to claim 18 wherein
said carbonyl compound is selected from the group consisting of terephthalic acid, isophthalic acid, napthalic acid, succinic acid, adipic acid, phthalic acid, glutaric acid, oxalic acid, dimethyl adipate, dimethyl phthalate, dimethyl terephthalate, dimethyl glutarate, oligomer thereof, and combinations of two or more thereof, and
said first glycol and second glycol are each independently selected from the group consisting of ethylene glycol, propylene glycol, isopropylene glycol, butylene glycol, 1-methyl propylene glycol, pentylene glycol, diethylene glycol, triethylene glycol, polyoxyethylene glycol, polyoxypropylene glycol, polyoxybutylene glycol and combinations of two or more thereof.

22. A process according to claim 20 wherein said carbonyl compound is terephthalic acid, ester thereof, oligomer thereof, or combinations of two or more thereof and said first glycol and second glycol are each ethylene glycol.

23. A process according to claim 22, wherein the mole ratio of terephthalate and isophthalate in said copolymer is 99.9:0.1 to 50:50.

24. A process according to claim 17 wherein said phosphorus compound is introduced into said process before, during, or subsequent to said contacting.

25. A process according to claim 22 wherein said phosphorus compound is introduced into said process before, during, or subsequent to said contacting.

26. A process according to claim 23 wherein said phosphorus compound is introduced into said process before, during, or subsequent to said contacting.

27. A process according to claim 17 wherein said phosphorus compound is introduced into said isophthalic acid or said substantially soluble isophthalic acid solution.

28. A process according to claim 26 wherein said phosphorus compound is introduced into said isophthalic acid or said substantially soluble isophthalic acid solution.

* * * * *